(12) United States Patent
Griffin et al.

(10) Patent No.: US 8,277,438 B2
(45) Date of Patent: Oct. 2, 2012

(54) GUIDE CATHETER WITH REMOVABLE SUPPORT

(75) Inventors: Stephen Griffin, San Jose, CA (US); Gregory E. Mirigian, Dublin, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 38 days.

(21) Appl. No.: 12/797,374

(22) Filed: Jun. 9, 2010

(65) Prior Publication Data

US 2010/0249754 A1    Sep. 30, 2010

Related U.S. Application Data

(63) Continuation of application No. 10/729,742, filed on Dec. 5, 2003, now Pat. No. 7,771,369.

(51) Int. Cl.
*A61M 25/00* (2006.01)
(52) U.S. Cl. ......... 604/524; 604/264; 604/523; 600/585
(58) Field of Classification Search .................. 600/585; 604/529
See application file for complete search history.

(56) References Cited

U.S. PATENT DOCUMENTS

| | | | |
|---|---|---|---|
| 3,169,527 A | 2/1965 | Sheridan | |
| 3,674,014 A | 7/1972 | Tillander | |
| 3,867,945 A | 2/1975 | Long | |
| 4,362,163 A | 12/1982 | Krick | |
| 4,402,684 A | 9/1983 | Jessup | |
| 4,601,713 A | 7/1986 | Fuqua | |
| 4,651,751 A | 3/1987 | Swendson et al. | |
| 4,739,768 A | 4/1988 | Engelson | |
| 4,790,831 A | 12/1988 | Skribiski | |
| 4,840,623 A | 6/1989 | Quackenbush | |
| 4,909,787 A | 3/1990 | Danforth | |
| 5,098,412 A | 3/1992 | Shiu | |
| 5,120,323 A | 6/1992 | Shockey et al. | |
| 5,122,125 A | 6/1992 | Deuss | |
| 5,231,546 A | 7/1993 | Shimada | |
| 5,244,619 A | 9/1993 | Burnham | |
| 5,279,565 A | 1/1994 | Klein et al. | |
| 5,308,342 A | 5/1994 | Sepetka et al. | |
| 5,317,527 A | 5/1994 | Britton et al. | |
| 5,327,891 A | 7/1994 | Rammler | |
| 5,334,171 A | 8/1994 | Kaldany | |
| 5,382,238 A | 1/1995 | Abrahamson et al. | |
| 5,496,292 A | 3/1996 | Burnham | |
| 5,569,218 A | 10/1996 | Berg | |
| 5,593,394 A | 1/1997 | Kanesaka et al. | |
| 5,599,325 A | 2/1997 | Ju et al. | |
| 5,614,217 A | 3/1997 | Chiprich et al. | |
| 5,647,846 A | 7/1997 | Berg et al. | |
| 5,662,621 A | 9/1997 | Lafontaine | |

(Continued)

FOREIGN PATENT DOCUMENTS

EP    0256478    2/1988

(Continued)

*Primary Examiner* — Jeffrey G Hoekstra
(74) *Attorney, Agent, or Firm* — Seager, Tufte & Wickhem, LLC

(57) ABSTRACT

Catheters such as guide catheters can be configured for delivery of devices to vasculature portions such as intracranial spaces while retaining a desired level of flexibility. A catheter having an elongate shaft can include removable support means that can provide column support to the elongate shaft. The elongate shaft can include anchoring means that releasably secure the removable support means. The catheter can be deployed within a patient's vasculature, followed by deploying the removable support means.

12 Claims, 9 Drawing Sheets

U.S. PATENT DOCUMENTS

| | | |
|---|---|---|
| 5,680,873 A | 10/1997 | Berg et al. |
| 5,681,296 A | 10/1997 | Ishida |
| 5,715,817 A | 2/1998 | Stevens-Wright et al. |
| 5,762,631 A | 6/1998 | Klein |
| 5,782,811 A | 7/1998 | Samson et al. |
| 5,792,116 A | 8/1998 | Berg et al. |
| 5,879,342 A | 3/1999 | Kelley |
| 5,882,347 A | 3/1999 | Mouris-Laan et al. |
| 5,897,536 A | 4/1999 | Nap et al. |
| 5,897,537 A | 4/1999 | Berg et al. |
| 5,911,715 A | 6/1999 | Berg et al. |
| 5,957,979 A | 9/1999 | Beckman et al. |
| 5,968,009 A | 10/1999 | Simán |
| 5,971,975 A | 10/1999 | Mills et al. |
| 6,004,310 A | 12/1999 | Bardsley et al. |
| 6,080,140 A | 6/2000 | Swaminathan et al. |
| 6,185,449 B1 | 2/2001 | Berg et al. |
| 6,210,396 B1 | 4/2001 | MacDonald et al. |
| 6,379,365 B1 | 4/2002 | Diaz |
| 6,471,678 B1 | 10/2002 | Alvarez de Toledo et al. |
| 6,508,804 B2 | 1/2003 | Sarge et al. |
| 6,579,221 B1 | 6/2003 | Peterson |
| 6,607,496 B1 | 8/2003 | Poor et al. |
| 6,730,037 B2 | 5/2004 | Jang |
| 6,873,868 B2 | 3/2005 | Furnish |
| 2001/0000041 A1 | 3/2001 | Selmon et al. |
| 2001/0041881 A1 | 11/2001 | Sarge et al. |
| 2002/0183781 A1 | 12/2002 | Casey et al. |
| 2003/0032974 A1 | 2/2003 | Leschinsky et al. |

FOREIGN PATENT DOCUMENTS

| | | |
|---|---|---|
| EP | 0277366 | 8/1988 |
| EP | 0439932 | 8/1991 |
| EP | 0467422 | 1/1992 |
| EP | 0680351 | 11/1995 |
| JP | 4-357923 | 12/1992 |
| JP | 2001-346883 | 12/2001 |
| WO | 92/19308 A1 | 11/1992 |
| WO | 03/037415 A1 | 5/2003 |

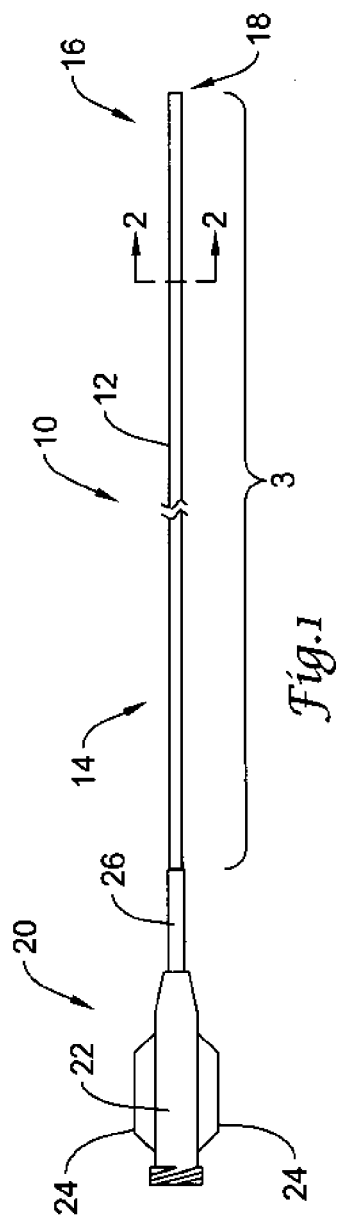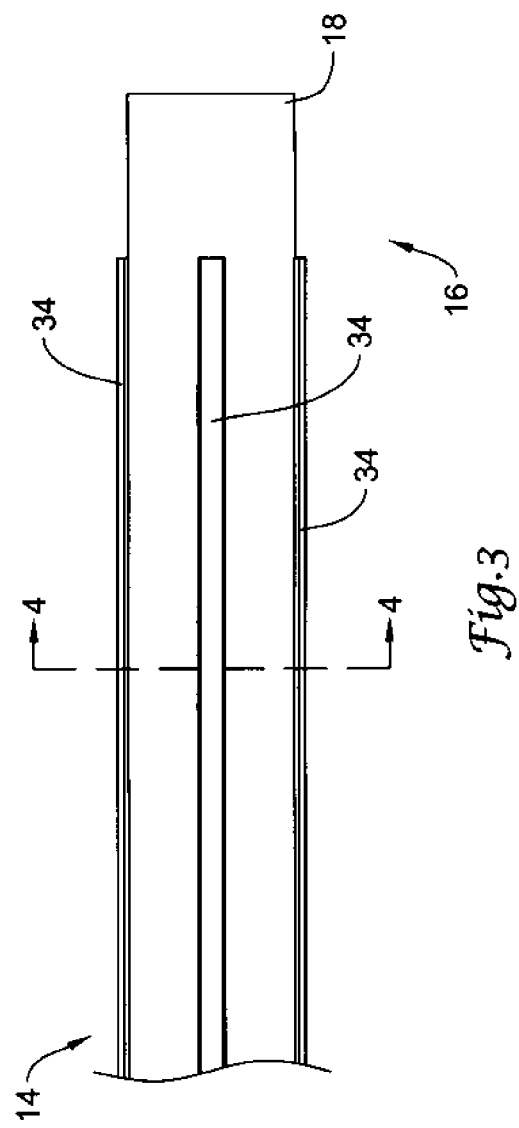

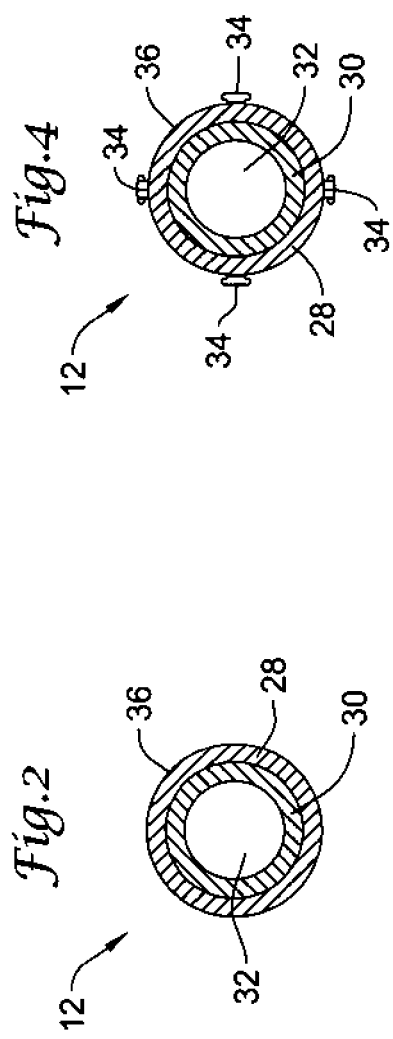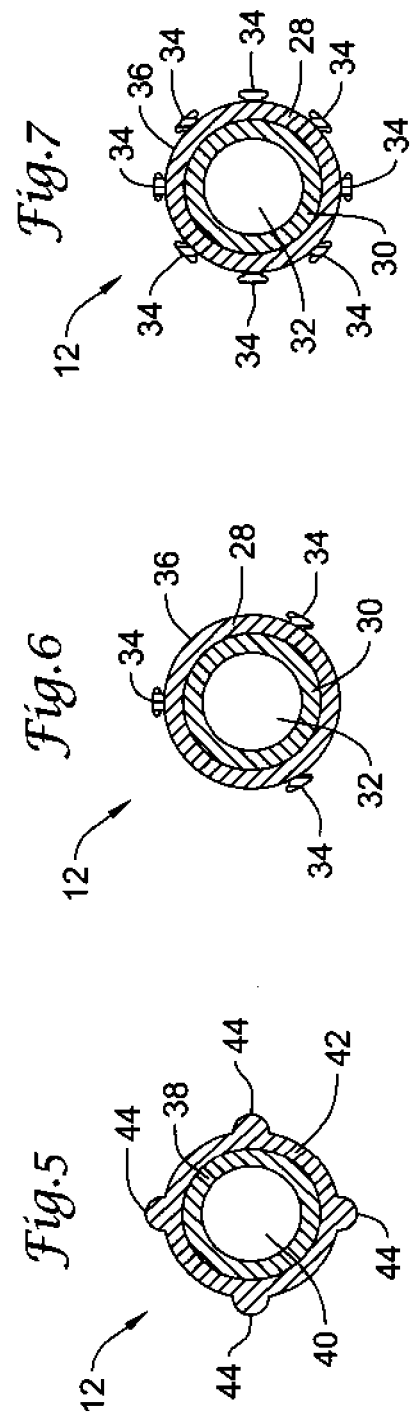

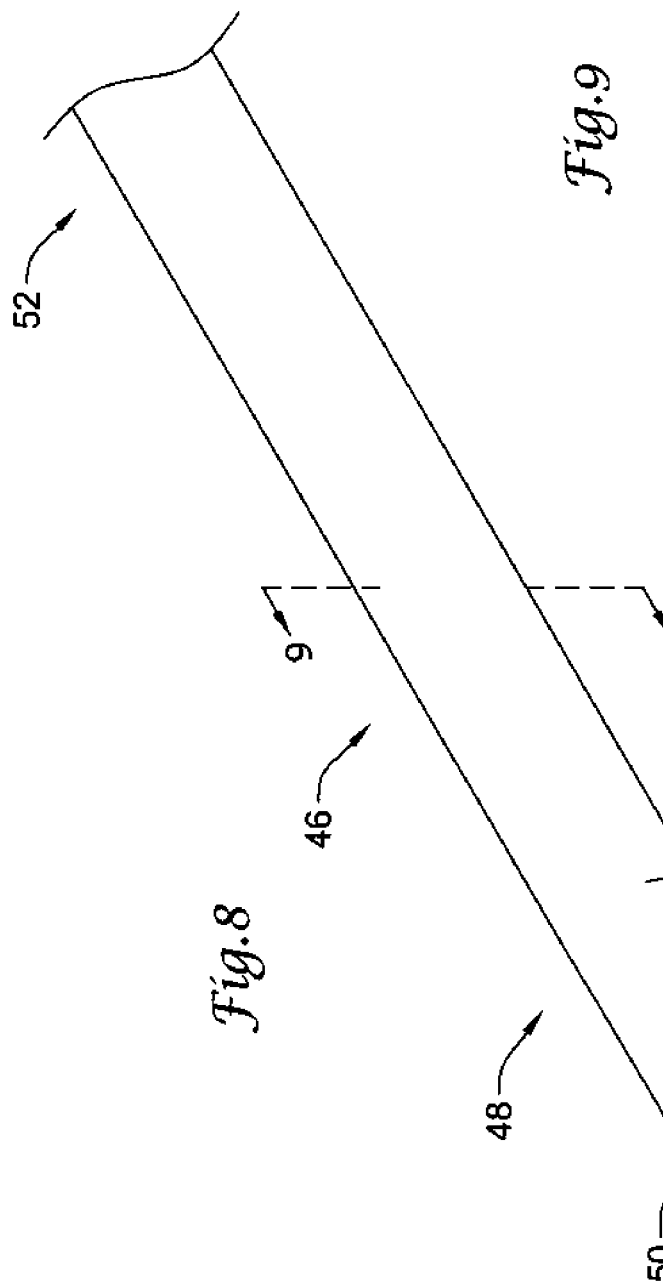
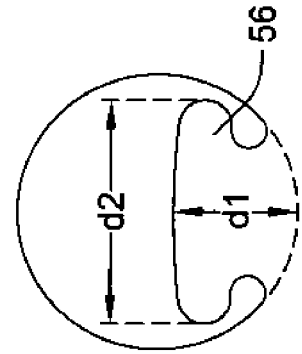

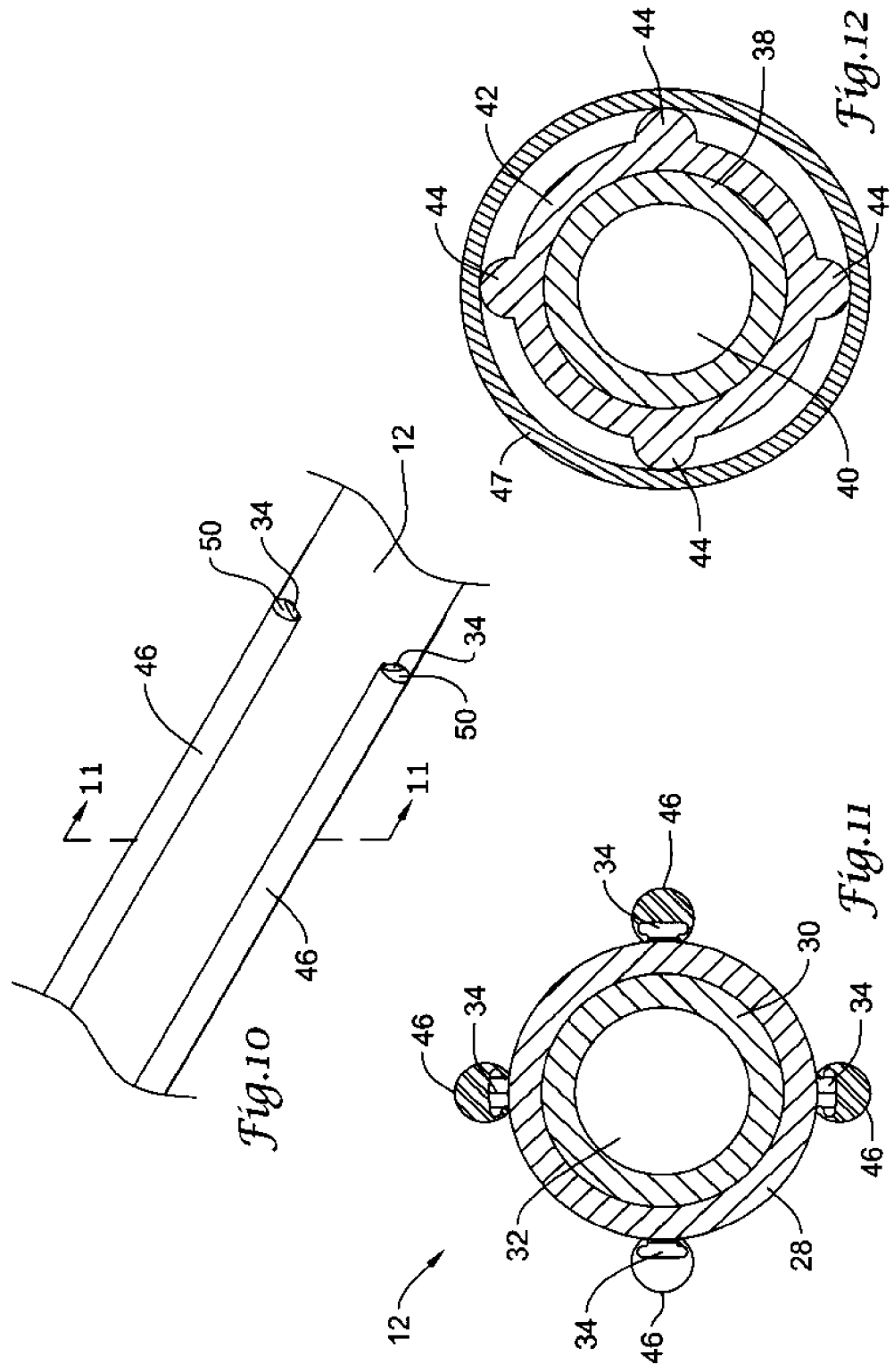

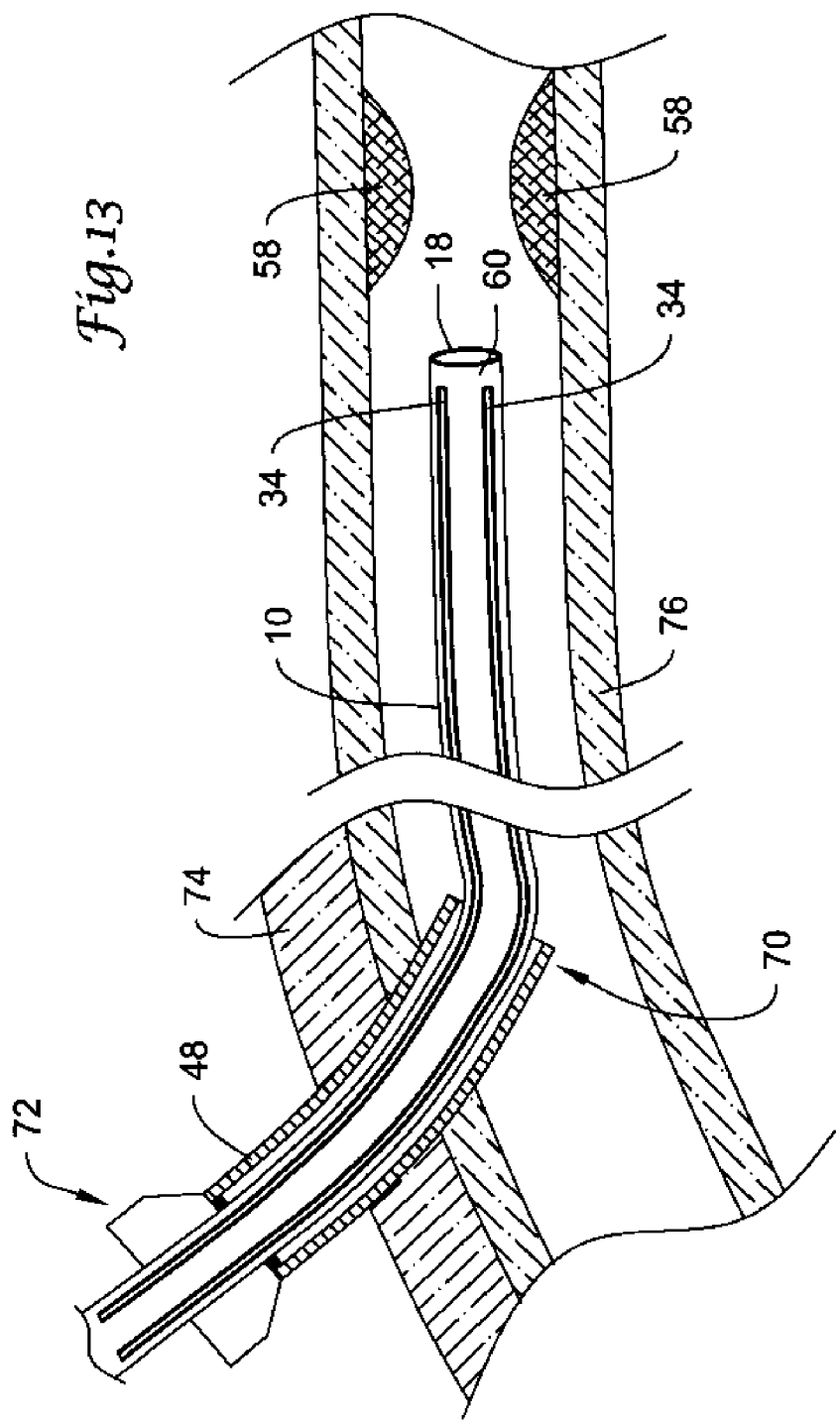

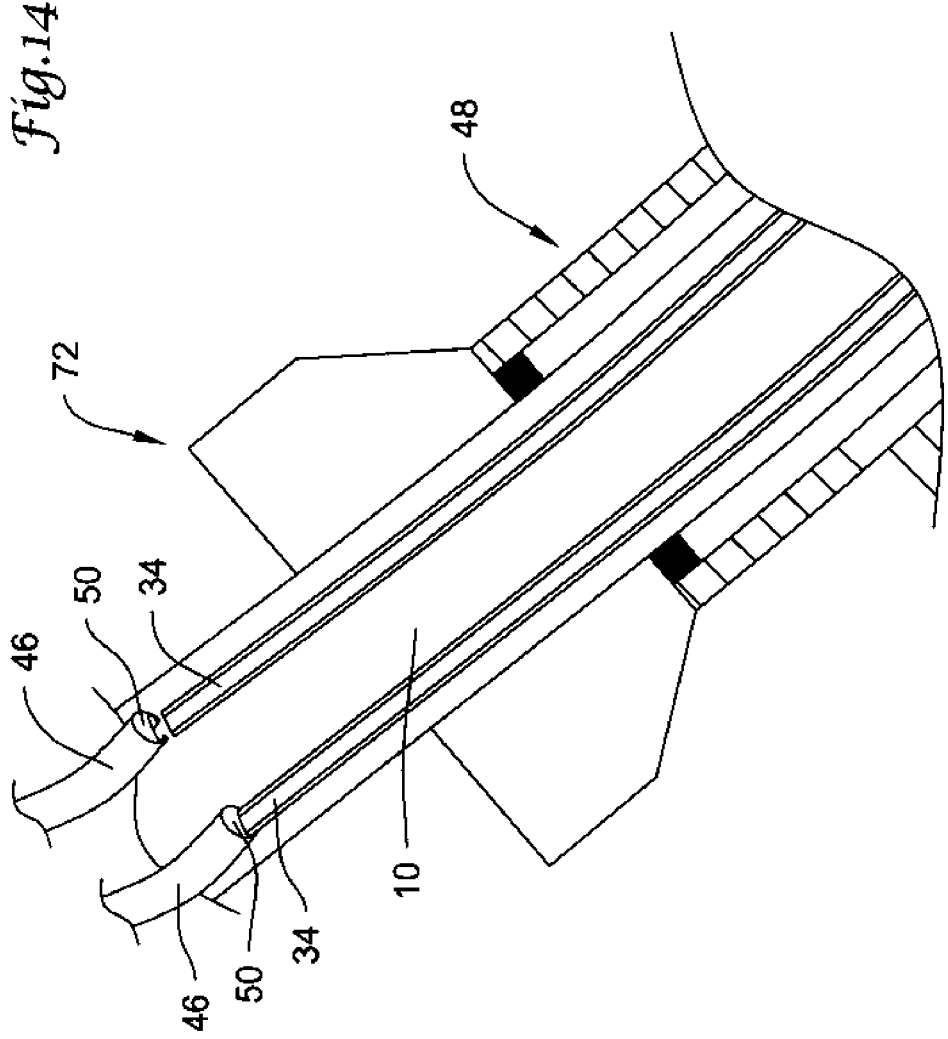

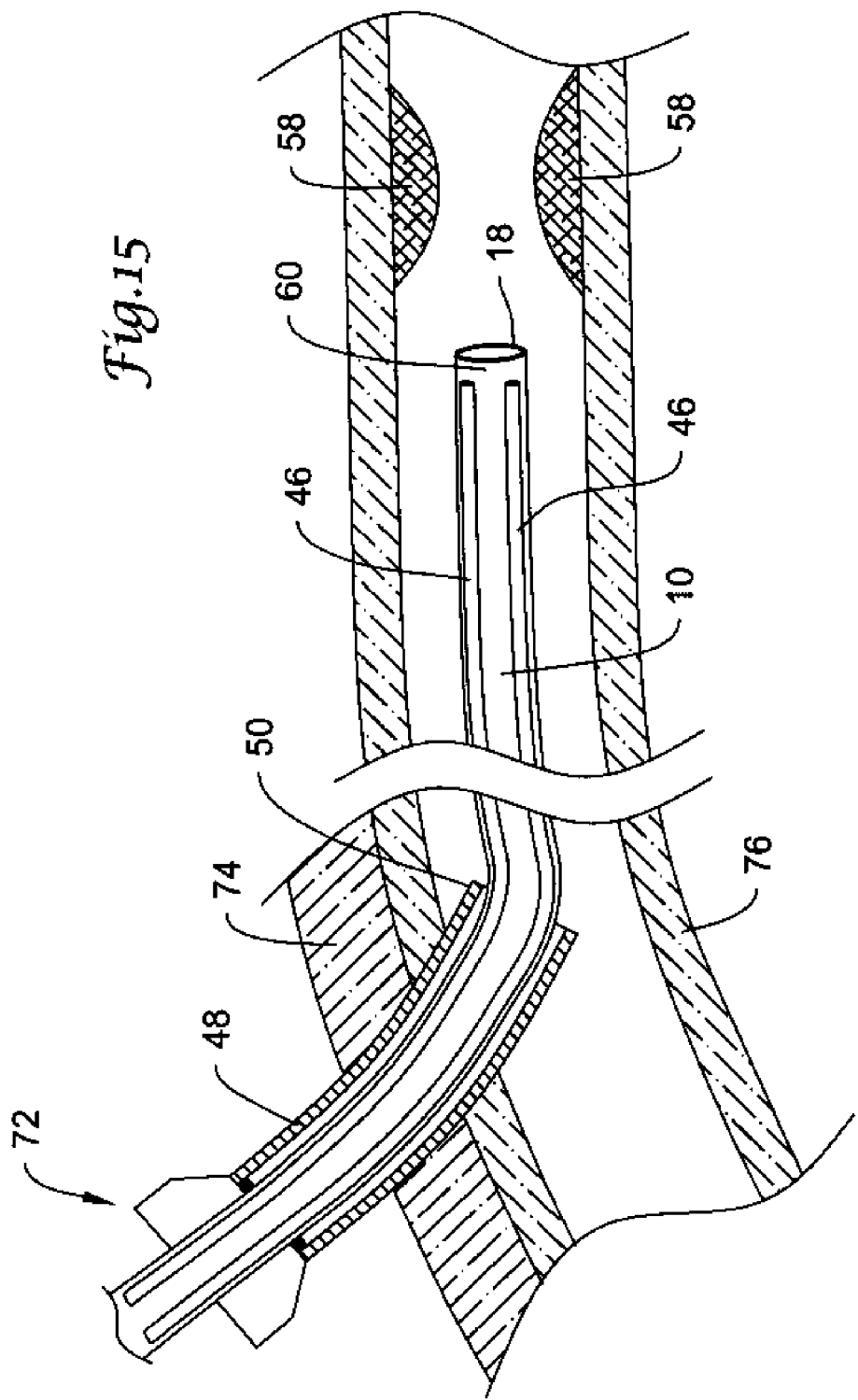

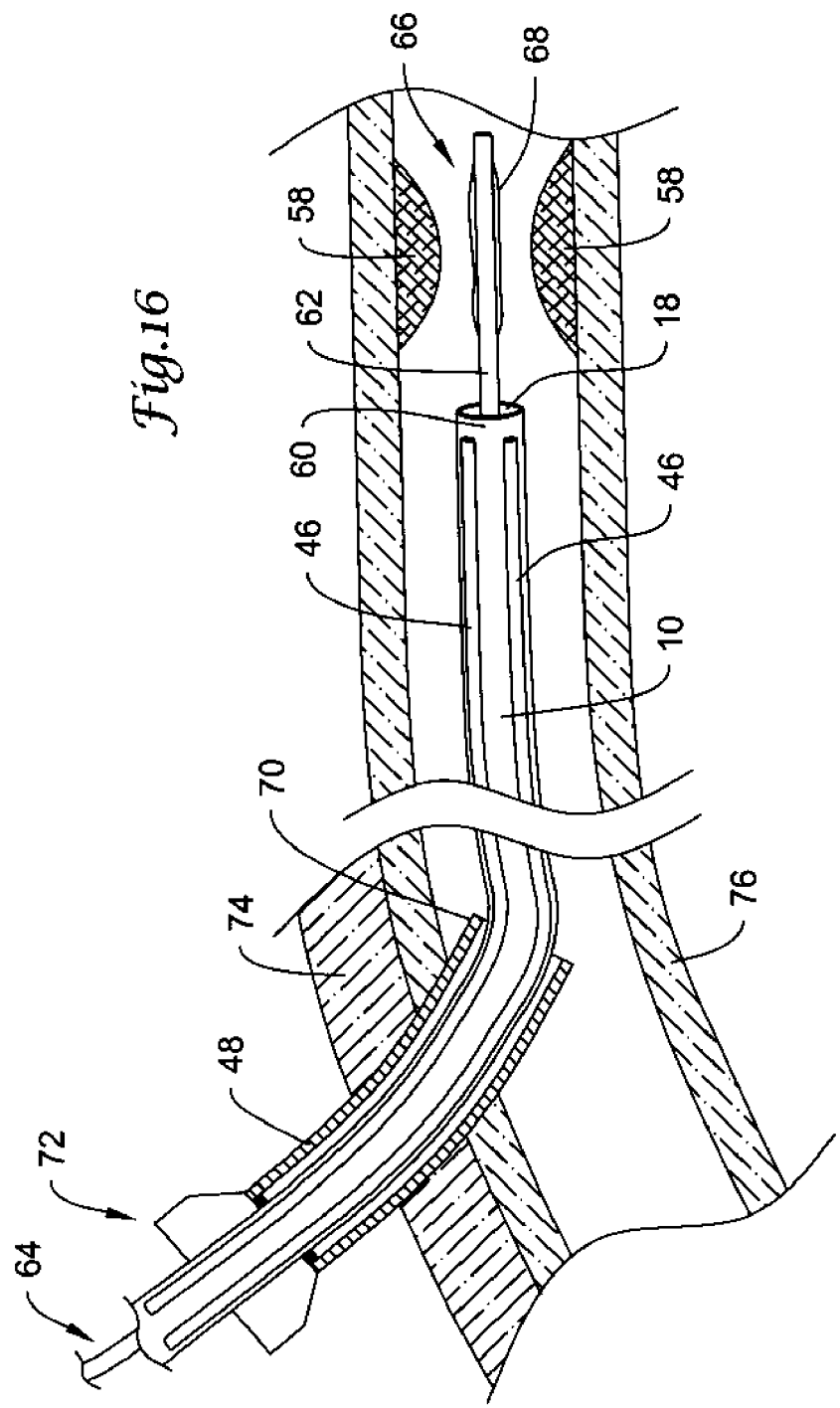

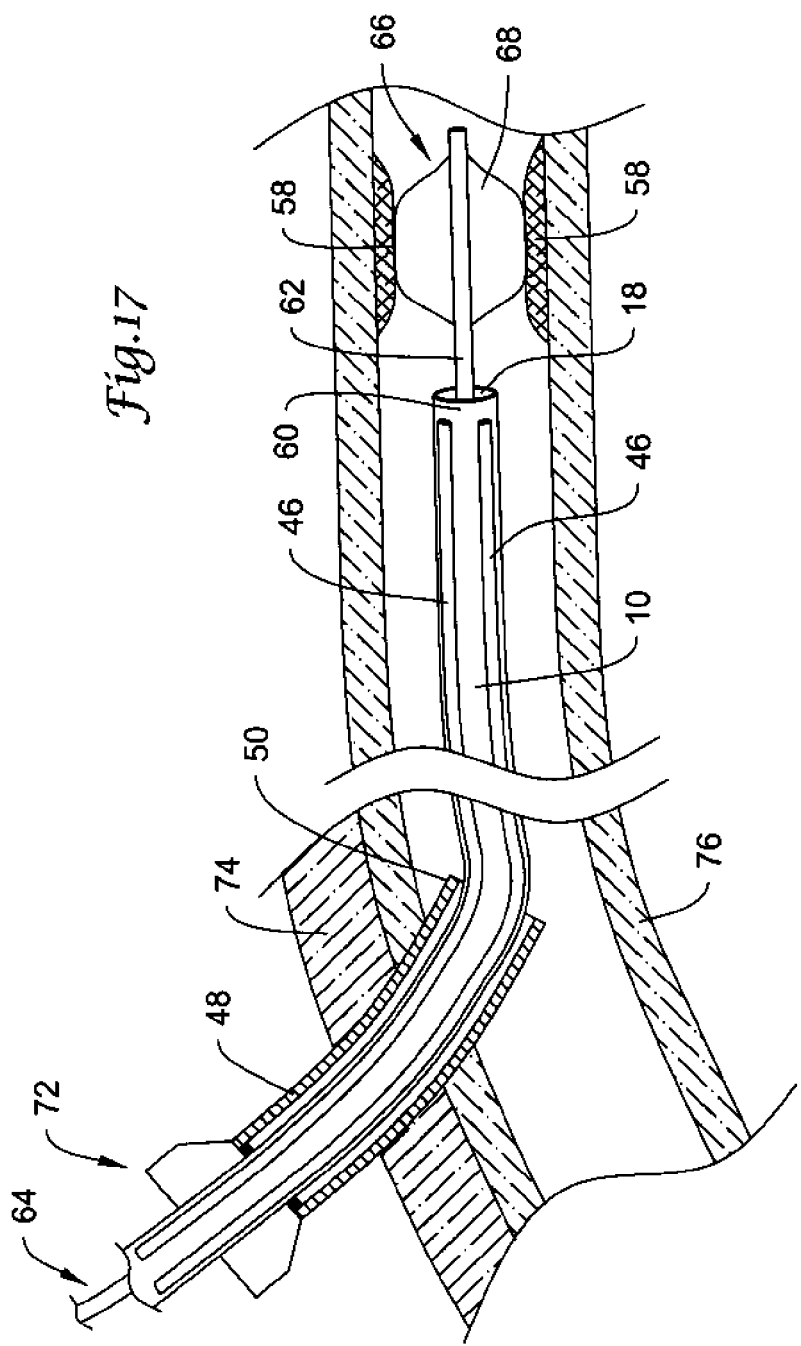

GUIDE CATHETER WITH REMOVABLE SUPPORT

CROSS-REFERENCE TO RELATED APPLICATIONS

This application is a continuation of U.S. application Ser. No. 10/729,742 filed Dec. 5, 2003, now U.S. Pat. No. 7,771,369, the entire disclosure of which is incorporated herein by reference.

TECHNICAL FIELD

The invention relates generally to elongate medical devices and more specifically to catheters. In particular, the invention relates to guide catheters that can include removable structure.

BACKGROUND

Catheters such as guide catheters can be subject to a number of often conflicting performance requirements such as flexibility, strength, minimized exterior diameter, maximized interior diameter, and the like. In particular, often times there is a balance between a need for flexibility and a need for strength or column support. If a catheter is sufficiently flexible to reach and pass through tortuous vasculature, the catheter may lack sufficient column strength to remain in position while, for example, subsequent treatment devices are advanced through the catheter.

Flexibility versus column strength can be a particular issue in intracranial access, which can require a catheter to pass through the aortic arch prior to making an essentially linear advancement to reach the brain, with again another perhaps tortuous path to a desired treatment site within a patient's head. Intracranial guide catheters have been configured to provide intracranial access to relatively soft elements, such as microcatheters and guide wires.

However, accommodating intracranial delivery of therapeutic elements such as stent delivery catheters and other balloon catheters presents a new set of challenges as these devices can be significantly stiffer and, therefore, can exert significantly greater radial forces on a guide catheter. As a result, guide catheters can be subject to backing out of particular vasculature such as the aortic arch and, thus, require repositioning.

Therefore, a need remains for catheters that are configured for delivering devices such as stent delivery catheters or other balloon catheters to intracranial locations. A need remains for a guide catheter that can provide sufficient column support while retaining a desired level of flexibility.

SUMMARY

The invention is directed to catheters configured for device delivery while retaining a desired level of flexibility. In particular, the invention is directed to catheters that provide a desired level of flexibility for advancing the catheter into a patient's vasculature yet can be provided with sufficient column support once the catheter has reached a desired position within the vasculature. If desired, the column support can be removed prior to removal of the catheter.

Accordingly, an illustrative embodiment of the invention can be found in a catheter that has an elongate shaft having a proximal region, a distal region, and an exterior surface extending therebetween. The catheter also includes removable support means for providing column support to the elongate shaft. The removable support means is disposed over a portion of the exterior surface of the elongate shaft.

Another illustrative embodiment of the invention can be found in a modular guide catheter that has an elongate shaft having a proximal region, a distal region and an exterior surface. A lumen extends from the proximal region to the distal region of the elongate shaft. The modular guide catheter includes a plurality of support tracks that are disposed on the external surface of the elongate shaft and that are generally axially aligned with the elongate shaft. The modular guide catheter also includes a plurality of support ribs that are configured to be removably disposed over the plurality of support tracks.

Another illustrative embodiment of the invention can be found in a method of deploying a catheter within a patient's vasculature. The catheter includes an elongate shaft having a proximal end, a distal end, an exterior surface extending therebetween and a plurality of support tracks axially disposed over the exterior surface. The catheter is advanced through the vasculature until the distal end of the elongate shaft reaches a desired position within the vasculature. One or more support ribs are disposed over one or more of the plurality of support tracks and are advanced over one or more of the plurality of support tracks to a position proximal of the distal end of the elongate shaft.

BRIEF DESCRIPTION OF THE FIGURES

The invention may be more completely understood in consideration of the following detailed description of various embodiments of the invention in connection with the accompanying drawings, in which:

FIG. 1 is a side elevation view of an intravascular catheter in accordance with an embodiment of the invention;

FIG. 2 is a cross-sectional view taken along line 2-2 of FIG. 1;

FIG. 3 is a closer view of a portion of the intravascular catheter of FIG. 1;

FIG. 4 is a cross-sectional view taken along line 4-4 of FIG. 3;

FIG. 5 is a cross-sectional view of an intravascular catheter in accordance with an embodiment of the invention;

FIG. 6 is a cross-sectional view of an intravascular catheter in accordance with an embodiment of the invention;

FIG. 7 is a cross-sectional view of an intravascular catheter in accordance with an embodiment of the invention;

FIG. 8 is a perspective view of a support rib in accordance with an embodiment of the invention;

FIG. 9 is a cross-sectional view taken along line 9-9 of FIG. 8;

FIG. 10 is a perspective view of a portion of the intravascular catheter of FIG. 3, including the support ribs as shown in FIG. 8;

FIG. 11 is a cross-sectional view taken along line 11-11 of FIG. 10;

FIG. 12 is a view of FIG. 5, with the addition of an external support sheath in accordance with an embodiment of the invention;

FIG. 13 is a schematic view of the intravascular catheter of FIG. 3, positioned through an introducer sheath within a patient's vasculature;

FIG. 14 is a schematic view of the proximal portion of the introducer sheath of FIG. 11, showing initial placement of the support ribs of FIG. 8;

FIG. 15 is a schematic view of the intravascular catheter of FIG. 13, with the support ribs advanced fully into position;

FIG. 16 is a schematic view of the intravascular catheter of FIG. 15, with the addition of a balloon catheter positioned proximate a lesion; and FIG. 17 is a schematic view of the intravascular catheter of FIG. 16, showing the balloon catheter with its balloon in an inflated position.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

FIG. 1 is a plan view of a catheter 10 in accordance with an embodiment of the invention. The catheter 10 can be one of a variety of different catheters, but is preferably an intravascular catheter. Examples of intravascular catheters include balloon catheters, atherectomy catheters, drug delivery catheters, diagnostic catheters and guide catheters. As illustrated, FIG. 1 portrays a guide catheter, but the invention is not limited to such. Except as described herein, the intravascular catheter 10 can be manufactured using conventional techniques and materials.

The intravascular catheter 10 can be sized in accordance with its intended use. The catheter 10 can have a length that is in the range of about 50 centimeters to about 100 centimeters and can have a diameter that is in the range of about 4F (French) to about 9F.

In the illustrated embodiment, the intravascular catheter 10 includes an elongate shaft 12 that has a proximal region 14, a distal region 16 and a distal end 18. A hub and strain relief assembly 20 can be connected to the proximal region 14 of the elongate shaft 12. The hub and strain relief assembly 20 includes a main body portion 22, a pair of flanges 24 designed to improve gripping, and a strain relief 26 that is intended to reduce kinking. The hub and strain relief assembly 20 can be of conventional design and can be attached using conventional techniques.

FIG. 2 is a cross-sectional view of the elongate shaft 12, taken along line 2-2 of FIG. 1. The elongate shaft 12 includes an outer layer 28 and an inner layer 30. Each of the outer layer 28 and the inner layer 30 can extend from the proximal region 14 of the elongate shaft 12 to the distal region 16 of the elongate shaft 12. The inner layer 30 defines a lumen 32 that extends through the elongate shaft 12.

In some embodiments, the elongate shaft 12 can optionally include a reinforcing braid or ribbon layer to increase particular properties such as kink resistance. If a reinforcing braid or ribbon layer is included, it can be positioned between the outer layer 28 and the inner layer 30. The optional reinforcing braid or ribbon layer can be provided in a configuration that provides adequate kink resistance without substantially increasing the overall profile of the elongate shaft 12, as the elongate shaft 12 can be provided with other means of column support, as will be discussed in greater detail hereinafter.

In some embodiments (not illustrated), the elongate shaft 12 can include one or more shaft segments having varying degrees of flexibility. For example, the elongate shaft 12 can include a proximal segment, an intermediate segment and a distal segment. In some embodiments, the elongate shaft 12 can also include a distal tip segment that can be formed from a softer, more flexible polymer. The elongate shaft 12 can include more than three segments, or the elongate shaft 12 can include fewer than three segments.

If the elongate shaft 12 has, for example, three segments such as a proximal segment, an intermediate segment and a distal segment, each segment can include an inner layer 30 that is the same for each segment and an outer layer that becomes increasingly more flexible with proximity to the distal end 18 of the elongate shaft 12. For example, the proximal segment can have an outer layer that is formed from a polymer having a hardness of 72D (Durometer), the intermediate segment can have an outer layer that is formed from a polymer having a hardness of 68D and the distal segment can be formed from a polymer having a hardness of 46D.

If the elongate shaft 12 has three segments, each of the segments can be sized in accordance with the intended function of the resulting catheter 10. For example, the proximal segment can have a length of about 35 inches, the intermediate segment can have a length that is in the range of about 2 inches to about 3 inches, and the distal segment can have a length that is in the range of about 1 inch to about 1.25 inches.

The inner layer 30 can be a uniform material and can define a lumen 32 that can run the entire length of the elongate shaft 12 and that is in fluid communication with a lumen (not illustrated) extending through the hub assembly 20. The lumen 32 defined by the inner layer 30 can provide passage to a variety of different medical devices, and thus the inner layer 30 can include, be formed from or coated with a lubricious material to reduce friction within the lumen 32. An exemplary material is polytetrafluoroethylene (PTFE), better known as TEFLON®. The inner layer 30 can be dimensioned to define a lumen 32 having an appropriate inner diameter to accommodate its intended use. In some embodiments, the inner layer 30 can define a lumen 32 having a diameter of about 0.058 inches and the inner layer 30 can have a wall thickness of about 0.001 inches.

The outer layer 28 can be formed from any suitable polymer that will provide the desired strength, flexibility or other desired characteristics. Polymers with low durometer or hardness can provide increased flexibility, while polymers with high durometer or hardness can provide increased stiffness. In some embodiments, the polymer material used is a thermoplastic polymer material. Some examples of some suitable materials include polyurethane, elastomeric polyamides, block polyamide/ethers (such as PEBAX®), silicones, and co-polymers. The outer layer 28 can be a single polymer, multiple layers, or a blend of polymers. By employing careful selection of materials and processing techniques, thermoplastic, solvent soluble, and thermosetting variants of these materials can be employed to achieve the desired results.

In particular embodiments, a thermoplastic polymer such as a co-polyester thermoplastic elastomer such as that available commercially under the ARNITEL® name can be used.

The outer layer 28 can have an inner diameter that is about equal to the outer diameter of the inner layer 30.

In some embodiments, the outer layer 28 can have an inner diameter in the range of about 0.0600 inches to about 0.0618 inches and an outer diameter in the range of about 0.0675 inches to about 0.0690 inches. Part or all of the outer layer 28 can include materials added to increase the radiopacity of the outer layer 28, such as 50% bismuth subcarbonate.

Turning to FIG. 3, a portion of elongate shaft 12 is illustrated in greater detail. In particular, elongate shaft 12 includes several axially aligned support tracks 34 that extend from the proximal region 14 of the elongate shaft 12 to the distal region 16 of the elongate shaft 12. A support track 34 can be considered to be generally axially aligned with the elongate shaft 12 if the support track 34 is generally parallel with a long axis of the elongate shaft 12. In some embodiments, the support tracks 34 extend distally to a position that is proximal of the distal end 18, thereby not interfering with the flexibility of the distal end 18. The function of the support tracks 34 will be discussed in greater detail hereinafter.

FIG. 4, which is a cross-sectional view taken along line 4-4 of FIG. 3, illustrates a particular profile of the support tracks 34 as well as a particular configuration employing four support tracks 34. As illustrated, the support tracks 34 are formed independently of the elongate shaft 12 and are subsequently attached to the outer surface 36 of the elongate shaft 12. In other embodiments, the support tracks 34 can be co-extruded with the elongate shaft 12.

The support tracks 34 can be formed from any suitable polymeric material. Examples of suitable polymeric materials include polyolefins, polymers that have been surface-treated to provide reduced friction, and fluoropolymers such as TEFLON®. The support tracks 34 can be formed having any suitable dimensions.

In some embodiments, each of the support tracks 34 has an overall length that is about the length of the catheter 10. In some embodiments, each of the support tracks 34 can have a length that is somewhat less than the length of the catheter 10. Each of the support tracks 34 can have a width that is in the range of about 0.004 inches to about 0.010 inches and a total depth relative to the outer surface 36 of the elongate shaft 12 that is in the range of about 0.006 inches to about 0.017 inches.

FIG. 4 shows an embodiment in which a total of four support tracks 34 are equidistantly radially spaced about the elongate shaft 12. The support tracks 34 can be spaced about ninety degrees apart. In some embodiments, the support tracks 34 do not have to be equidistantly spaced. In such embodiments, there can be flexibility or curvability advantages to grouping the support tracks 34 along one side of the elongate shaft 12.

In other embodiments, either less than four or more than four support tracks 34 can be used, as illustrated, for example, in FIGS. 6 and 7. In FIG. 6, a total of three support tracks 34 have been secured to the exterior surface 36 of the elongate shaft 12. As shown, the support tracks 34 are equally spaced about 120 degrees apart. In FIG. 7, a total of eight support tracks 34 are spaced about the outer surface 36 of the elongate shaft 12. In this embodiment, the support tracks 34 can be spaced about forty-five degrees apart. In other embodiments, the support tracks 34 do not have to be equidistantly spaced. In other embodiments, there can be a total of one, two, three, four, five, six, seven, eight or more support tracks 34 spaced about the outer surface 36 of the elongate shaft 12.

In each of these embodiments, the support tracks 34 can be formed separately and then attached to the outer surface 36 of the elongate shaft 12. In some embodiments, the support tracks 34 can be heat bonded to the exterior surface 36 of the elongate shaft 12. In some embodiments, the support tracks 34 can be adhesively attached to the exterior surface 36 of the elongate shaft 12 using any suitable adhesive, such as a cyanoacrylate or an epoxy.

FIG. 5 illustrates another embodiment in which a catheter shaft has an inner layer 38 defining a lumen 40. The inner layer 38 can be constructed and dimensioned similar to that discussed above with respect to the inner layer 30. The catheter shaft also has an outer layer 42 that can be constructed from any suitable polymer, as discussed previously with respect to the outer layer 28. However, in the illustrated embodiment, the outer layer 42 includes several support tracks 44 that are integrally formed with the outer layer 42. The outer layer 42 can be extruded or otherwise formed to include the support tracks 44.

In FIG. 5, the support tracks 44 have a substantially semi-circular profile. FIGS. 4, 6 and 7, however, show an embodiment in which the support tracks 34 have an ovoid cross-sectional profile having a minor dimension that is perpendicular to the exterior surface of the elongate surface and a major dimension that is perpendicular to the minor dimension. The major dimension can vary as a function of distance from the exterior surface of the elongate shaft 12, with the major dimension being minimized at a position proximate the exterior surface 36 of the elongate shaft 12 and maximized at a position radially displaced from the exterior surface 36 a distance equal to or less than the minor dimension.

The support tracks 34 as described herein are configured to complement a support rib 46 as illustrated, for example, in FIG. 8. FIG. 8 is a perspective view of a support rib 46 that has a distal region 48, a distal end 50 and a proximal region 52. The support rib 46 has an outer surface 54 and an inner surface 56. A comparison of the inner surface 56 to the support tracks 34 as previously described illustrates that the inner surface 56 of the support rib 46 is complementary to the cross-sectional profile of the support tracks 34.

FIG. 9 is a cross-sectional view of the support rib 46, taken along the line 9-9 of FIG. 8. The inner surface 56 can be seen to have a minor dimension d1 that is perpendicular to a long axis of the support rib 46 and a major dimension d2 that is perpendicular to the minor dimension d1. As discussed above with respect to the support track 34, the major dimension can vary as a function of distance from the exterior surface of the elongate shaft 12. As a result of the complementary profiles of the inner surface 56 of the support rib 46 and the outer surface of the support track 34, axial movement of the support rib 46 with respect to the support track 34 is permitted, while relative radial movement is restricted.

FIG. 10 illustrates a portion of the elongate shaft 12 in which several support ribs 46 have been positioned over the support tracks 34. FIG. 11 is a cross-sectional view taken along line 11-11 of FIG. 10. This view is essentially the same as FIG. 4, with the addition of four support ribs 46, with one support rib 46 positioned over each of the four support tracks 34.

The support ribs 46 can be made of any suitable polymeric material. In some embodiments, the support ribs 46 can be made of a suitable polymeric material having a low coefficient of friction. Examples of suitable polymeric materials include fluorinated polyethylenes such as polytetrafluoroethylene. The support ribs 46 can be formed to have any suitable dimensions. The support ribs 46 can be about the same length as the catheter 10, or the support ribs 46 can be longer than the catheter 10 in order to provide handling advantages.

In some embodiments, the support ribs 46 can have an overall length that is in the range of about 80 centimeters to about 150 centimeters. The support ribs 46 can have an overall diameter that ranges from about 0.010 inches to about 0.020 inches. The dimensions d1 and d2 can range from about 0.004 inches to about 0.008 inches and from about 0.006 inches to about 0.015 inches, respectively.

In some embodiments, a variety of support ribs 46 can be provided, each having a different diameter. If a greater level of column support is desired, a physician or other professional can use one or more support ribs 46 that have a larger diameter and, thus, can provide a greater level of support. If less column support is needed, or if the patient has a relatively constricted vasculature, support ribs 46 having a smaller diameter can be used. In some embodiments, a physician or other professional can use a greater number of support ribs 46 or a lesser number of support ribs 46. For example, if the elongate shaft 12 includes four support tracks 34, the physician has the option to use no support ribs 46, one support rib 46, two, three or even four support ribs 46, depending on the desired level of support.

It should be noted that the support ribs 46 are not limited to the inner surface 56 profile illustrated. In some embodiments, the inner surface 56 can have a rectangular profile, with a relatively reduced dimension perpendicular to the long axis of the support rib 46 and a relatively greater dimension perpendicular to the relatively reduced dimension. In other embodiments, the inner surface 56 can have any other profile that permits axial movement of the support rib 46 with respect to the support track 34, while restricting or eliminating relative radial movement.

FIG. 12 illustrates a particular embodiment of the invention employing a support sheath 47, rather than the distinct support ribs 46 previously discussed. The support sheath 47 can be sized to have an inner diameter that is approximately the same as the outer diameter of the outer layer 42, including the support tracks 44. The support sheath 47 can have an inner diameter that is slightly larger than the aforementioned outer diameter, in order to reduce friction in advancing the support sheath 47. The support sheath 47 also can be used in conjunction with the ovoid-shaped support tracks 34 as illustrated in the other Figures.

The support sheath 47 can be formed from any suitable polymeric material, such as a polyolefin. In some embodiments, the inner surface of the support sheath 47 can be formed from or coated with a material having a low coefficient of friction. Polytetrafluoroethylene is an exemplary material.

FIGS. 13-17 demonstrate an intended use of the catheter 10. In FIG. 13, an introducer sheath 48 having a distal end 70 and a proximal end 72 has been extended through a patient's tissue 74 into the patient's vasculature 76 as is well known in the art. The catheter 10 has been inserted into the proximal end 72 of the introducer sheath 48 and has been advanced to a position near a desired treatment site, such as a lesion 58. When introduced, the catheter 10 includes the aforementioned support tracks 34, but does not include the support ribs 46.

Once the catheter 10 has been appropriately positioned, the support ribs 46 can be advanced over the support tracks 34 to provide a desired level of column support prior to introducing any treatment devices through the catheter 10. FIG. 14 illustrates the proximal end 72 of the introducer sheath 48. The support ribs 46 are configured such that they can be slid axially over the support tracks 34. Once the distal ends 50 of each support rib 46 is started over the corresponding support track 34, the support ribs 46 can be advanced until they reach the distal end 60 of the support tracks 34. FIG. 15 shows the catheter 10 with the support ribs 46 fully advanced over the support tracks 34.

At this point, the catheter 10 is configured for passage of a treatment device such as a balloon catheter, stent delivery catheter, atherectomy device or the like. The addition of the support ribs 46 provides the catheter 10 with additional column support. FIG. 16 illustrates the catheter 10 including the support ribs 46 positioned within the patient's vasculature 76. In the illustrated embodiment, a balloon catheter 62 having a proximal region 64 and a distal region 66 has been positioned within the lumen 32 extending through the catheter 10.

The proximal region 64 of the balloon catheter 62 extends proximally from the patient so that the balloon catheter 62 can be controlled as is known in the art. The distal region 66 is positioned distal of the distal end 18 of the catheter 10 such that it is proximate a treatment region such as the lesion 58. The distal region 66 of the balloon catheter 62 includes an inflatable balloon 68. As illustrated in FIG. 17, the inflatable balloon 68 can be inflated to compress the lesion 58.

While not explicitly illustrated, subsequent treatment can include atherectomy, should the lesion 58 not be sufficiently compressed. Other possible subsequent treatments include compressing the lesion 58 with a different diameter inflatable balloon or positioning and deploying a stent. Once the physician has determined that no subsequent treatments are necessary, the support ribs 46 can be withdrawn proximally while the catheter 10 remains within the patient's vasculature 56. Alternatively, the catheter 10 can be withdrawn proximally from the patient while the support ribs 46 remain in position on the support tracks 34.

In some embodiments, part or all of the catheter 10 can include a lubricious coating. Lubricious coatings can improve steerability and improve lesion crossing capability. Examples of suitable lubricious polymers include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers can be blended among themselves or with formulated amounts of water insoluble compounds (including some polymers) to yield coatings with suitable lubricity, bonding, and solubility. In some embodiments, a distal portion of the catheter can be coated with a hydrophilic polymer, while the more proximal portions can be coated with a fluoropolymer.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What we claim is:
1. A catheter, comprising:
an elongate catheter shaft having a proximal portion and a distal portion;
wherein the catheter shaft includes an inner layer and an outer layer extending around the entire circumference of the inner layer;
a support track radially projecting from an outer surface of the outer layer of the shaft; and
a support rib for providing column strength to the catheter shaft, the support rib having a cutout formed therein, the cutout being disposed over the support track;
wherein the support track has a cross-sectional profile that is complementary to the shape of the cutout and is configured to permit the support rib to move longitudinally along the support track while limiting radial movement of the support rib relative to the support track.

2. The catheter of claim 1, wherein the support rib includes a fluorinated polyethylene polymer.

3. The catheter of claim 2, wherein the fluorinated polyethylene polymer comprises polytetrafluoroethylene.

4. The catheter of claim 1, further comprising one or more additional support tracks radially projecting from the outer surface of the outer layer of the shaft.

5. The catheter of claim 4, further comprising one or more additional support ribs disposed over the one or more additional support tracks.

6. The catheter of claim 1, wherein the support track has a solid cross-section.

7. The catheter of claim 1, further comprising a reinforcing member disposed between the inner layer and the outer layer.

8. The catheter of claim 7, wherein the reinforcing member includes a braid.

9. The catheter of claim 1, wherein the support track extends from the proximal portion of the shaft to the distal portion of the shaft.

10. The catheter of claim 1, wherein the shaft includes a distal end, and wherein the support track extends from the proximal portion of the shaft to a position proximal of the distal end of the shaft.

11. A catheter, comprising:
an elongate catheter shaft having a proximal portion, a distal portion, and an outer surface;
a support track radially projecting from the outer surface of the shaft;
a support rib for providing column strength to the catheter shaft, the support rib having a cutout formed therein, the cutout being disposed over the support track;
wherein the support track has a cross-sectional profile that is complementary to the shape of the cutout and is configured to permit the support rib to move longitudinally along the support track while limiting radial movement of the support rib relative to the support track; and
wherein the support track, the support rib, or both are free of echogenic microbubbles.

12. The catheter of claim 11, wherein the support rib is free of echogenic microbubbles.

* * * * *